United States Patent [19]

Simmet et al.

[11] Patent Number: 4,865,589
[45] Date of Patent: Sep. 12, 1989

[54] INSTRUMENT FOR THE TRANSFER OF MATERIALS SUCH AS SPERM AND EMBRYOS

[76] Inventors: Ludwig Simmet, Prof. Dietl-Weg 1, D-8300 Landshut; Ludwig O. Simmet, Hopfenfeld 1, D-8311 Zweikirchen, both of Fed. Rep. of Germany

[21] Appl. No.: 87,226

[22] Filed: Aug. 20, 1987

[30] Foreign Application Priority Data

Apr. 22, 1987 [DE] Fed. Rep. of Germany ... 8705864[U]

[51] Int. Cl.$^4$ ............................................. A61M 5/00
[52] U.S. Cl. ................................... 604/171; 604/232; 604/235; 604/906
[58] Field of Search .......... 604/171, 232, 235, DIG. 1

[56] References Cited

U.S. PATENT DOCUMENTS

| | | | |
|---|---|---|---|
| 899,728 | 9/1908 | Graham | 604/DIG. 1 |
| 2,503,341 | 4/1950 | Kissileff | 604/DIG. 1 |
| 2,572,155 | 10/1951 | Hoyt | 604/DIG. 1 |
| 2,616,422 | 11/1952 | Jones | 604/DIG. 1 |
| 2,712,315 | 7/1955 | Rice | 604/DIG. 1 |
| 3,507,281 | 4/1970 | Cassou | 604/232 |
| 3,595,230 | 7/1971 | Suyeoka | 604/171 |
| 3,910,275 | 10/1975 | Babey et al. | 604/DIG. 1 |

Primary Examiner—C. Fred Rosenbaum
Assistant Examiner—Kathleen A. Daley
Attorney, Agent, or Firm—Panitch Schwarze Jacobs & Nadel

[57] ABSTRACT

The invention provides an universally applicable transfer device for material such animal sperm or embryos to be implanted, having a catheter covered by a sleeve which is generally discarded after use and which is detachably held in place by a clamp, more especially an eccentric gripping device at the proximal end of the catheter. The design of the sleeve end is unimportant. At the distal end the sleeve tapers conically and externally it has a shaped member securing the conical form and a rounded form. The shaped member is mounted on the wall material of the sleeve. The external shaped member may be supplemented by an internal shaped member so that the distal sleeve end is gripped between the two. A cutting means integrated in the device ensures that the cartridges are cut accurately in the desired plane.

13 Claims, 3 Drawing Sheets

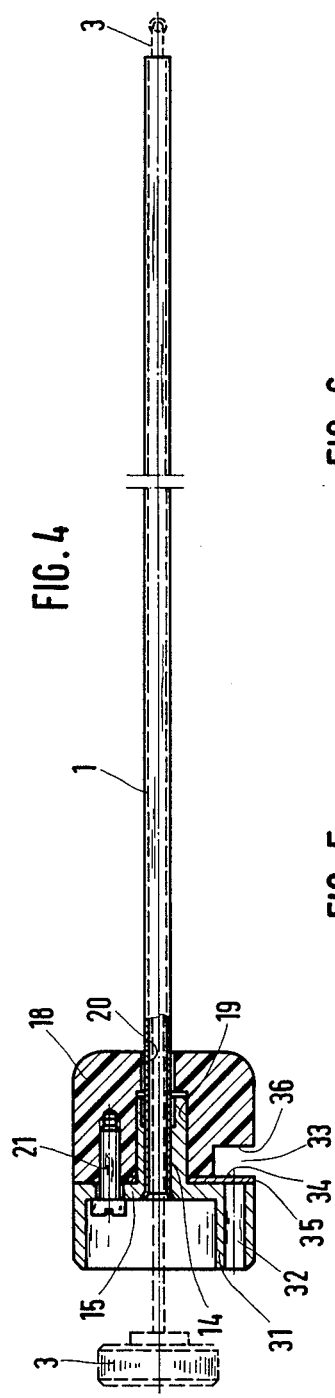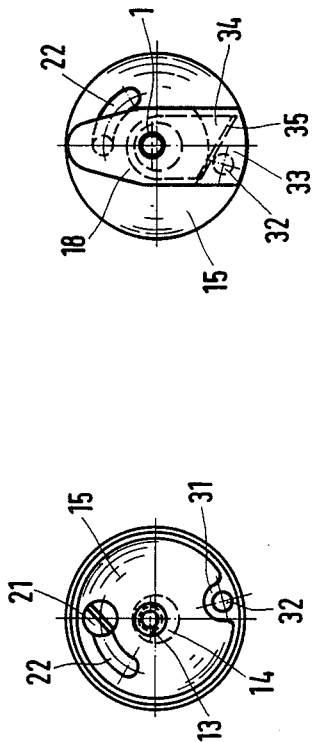

INSTRUMENT FOR THE TRANSFER OF MATERIALS SUCH AS SPERM AND EMBRYOS

BACKGROUND OF THE INVENTION

The invention relates to transfer devices for the administration of materials, as for example for sperm in artificial insemination consisting of a hollow cylindrical catheter open at both ends into which a tubular cartridge of material to be administered may be inserted at the distal or proximal end and a plunger may be inserted from the proximal end to force out the cartridge contents, and a replaceable tubular sleeve adapted to be slid onto the catheter, which has its proximal end detachably secured to the proximal end of the catheter, has a port for the emergence of the material to be administered and is tapered at its distal end and the latter and is provided with a radially symmetrical shaped member having a longitudinal passage therein. Such transfer devices are more especially but not exclusively used for veterinary purposes for artifical insemination or embryo transfer. The first step is for the throw-away sleeve, which is usually made of plastic and tapers conically towards its distal tip conically, to be put on, whereafter the cartridge with the material to be administered is then inserted into the catheter from the proximal end and then, after introduction of the transfer device into the vagina of a cow, for instance, the material is expelled by the plunger. The cartridge may also be inserted from the front prior to putting on the sleeve. The transfer device is suitable for medicaments in a liquid or paste form.

In addition to ampules plastic tubes sealed at both ends are available in various sizes and which have at least two standard diameters. Accordingly thicker or thinner catheters and conical tips having a larger or smaller end opening are required. Sleeves with large and small diameters are conventional.

The attachment of such throw-away sleeves frequently give rise to difficulties.

For the attachment at the distal end a proposal has been made for a design of the initially mentioned type in FIG. 3 of the German unexamined specification 3,106,306, in which case the shaped member is bonded at the front into sleeve and is drawn with the latter onto the catheter. During use there is then the danger of the piston, which strikes the inner cone of the shaped member so as to press forwards and press out the contents of the cartridge, being broken off and being lost in the organ into which the transfer is being made. Such pistons are frequently in the form of small balls—as sealing balls of the cartridge or in the case of a plunger with a spherical tip—of for instance 3 mm in diameter, which are inserted forwards into the cartridge and extrude the contents thereof. When the ball in the end strikes the oblique conical surface it will exert its thrust thereon.

There has been a proposal (see the German patent 2,729,428) to attach the sleeve at the proximal end of the catheter by having a conically flared part of the catheter at this end so that the proximal sleeve end, which is slit for 3 to 4 cm for this purpose, may be slipped onto this end, at which position the sleeve may be clamped in place on the cone with the aid of a retainer ring drawn over it. In accordance with another design in this patent there is stepped helical rib at the proximal end of the catheter onto which the sleeve is screwed. In this case the sleeve may be plain and not slit at the proximal end.

The large number of different cartridges, more especially sperm cartridges and the different diameters of catheter make it necessary for the veterinary surgeon to have a stock of different transfer devices or even only different sleeves, which are drawn over the catheter as a casing. It may well happen that he has the unfortunate experience of seeing that he has the wrong type of sleeve or the wrong transfer device with him. This is more especially likely if it he has to use different cartridges, as is frequently the case with sperm.

SUMMARY OF THE PRESENT INVENTION

One object of the invention is to improve upon the prior art apparatus. In order to achieve particular part of the object of the invention intended to provide a more secure location of both thick and thin cartridges without the shaped member being dislodged by the piston the sleeve is attached at the distal end and the longitudinal passage in the shaped member accepts the sleeve so that the latter is within the shaped member and the wall face of its longitudinal passage is conically tapered in alignment with the outer wall face of the sleeve. Owing to the fact that the shaped member when put in place is seated externally on the sleeve it is in fact not possible for the piston, which may for instance be spherical, moving in the cone and pressing internally on the conical part of the sleeve itself, to dislodge this shaped member from the sleeve. On the other hand in the case of this design as well of the shaped member it is possible to provide a round distal end which favors simple and risk-free introduction of the transfer device into, for instance, the body of an animal.

In accordance with a particularly preferred feature of the invention the distal end of the sleeve is gripped in the gap between the outer shaped member and the inner shaped member, something which is particularly simple to arrange for in comparison with an adhesive bond. The shaped members may be extended towards the distal end by non-conical parts so that it is then simple to have an externally rounded form and to have a coupling between the two shaped members, more especially in this non-conical part. According to a further feature of the invention the coupling means includes a detent coupling mechanism with which the combined shaped member is firmly secured to the end of the sleeve so that, like the sleeve, it is only intended for use once over. Alternative possibilities would be a screw connection or a bayonet joint. In accordance with a further feature of the invention the external shaped member and internal shaped member have terminal faces which steplessly merge into each other. This feature may be readily achieved by having a connection which is rigid in the axial direction. There is then a smooth front face of the two shaped members taken as a whole.

In accordance with a further feature of the invention the sleeve material may originally be cylindrical and then be conically deformed by clamping it in the conical gap in the end part of the sleeve. For manufacture the sleeve material may then be cut from running lengths.

It is furthermore possible for the wall thickness of the internal shaped member to decrease towards the end remote from the distal end between its conical external face and its conical inner face. This measure is to ensure the smallest possible size of the step at the beginning of the internal shaped member so that the inserted cartridge extends into the conical longitudinal passage of the internal shaped member and does not foul its end face.

The design with external and internal shaped members leads to a very firm attachment of the combined shaped member to the sleeve so that just as is the case of the exclusive use of the external shaped member, detachment of the latter from the sleeve is practically out of the question.

In accordance with a further part of the invention it is possible to have a clamping chuck in the form of an eccentric gripping device, such as a chuck or collet with jaws, in order to press the rear edge of the sleeve against the outer side of the catheter irrespectively of whether the sleeve end is slit or not so. By the right selection of a suitably small diameter of the catheter it is possible to put on any sleeve with a conventional size. It is possible for the eccentric clamping device to consist of part of the catheter which is in the form of a body of revolution, and at an external step-like change in diameter is set back from the rest of the catheter, which is also externally in the form of a body of revolution, and of an arresting member rotatably placed on the eccentric set back part, same having a two-part hole, of which the first part, that is on the eccentric set back part of the catheter, has the same diameter as it with the addition of a gap to allow sliding, and whose second part has a diameter corresponding to the external diameter of the remaining catheter plus a gap at least equal to the thickness of the sleeve wall, is offset in relation to the first part eccentrically with parallel axes and adjoins the first part in the direction of the distal side. Such an eccentric chuck or collet causes a local pressing effect on the catheter wall when slightly turned and thus secures the sleeve at this point.

In accordance with a further feature of the invention the eccentrically set back part of the catheter is made up of a cylindrical tubular member firmly locked on the catheter and having an unequal wall thickness. This tubular member, which usually may be used as a handle, may be conveniently made of plastic or metal and is bonded, welded or screwed onto the catheter. The tubular member may have a flange in which a track is formed and the arresting member may have the form of a rotary handle and have an axial projection which fits into the track of the flange, and the ends pointing in the directions of turning limits the angle of turning of the arresting member. This means that the range of turning of the eccentric is limited so that the opening setting is defined and the closing direction there is an upper limit to the pressing force on the catheter.

It is furthermore possible for the flange to have a retainer hole which is open at both its ends and is parallel to the axis and a knife is provided on the arresting member which on twisting of the arresting member is drawn along one of the Openings or ends of the retainer hole. The knife may be arranged in the end plane of the arresting member adjacent to the flange and under the knife there is a recess with an extent corresponding to the distance moved under the retainer hole on twisting of the arresting member, the floor of the recess forming a radial abutment face. These features enable the design of the eccentric clamping device to be used in addition for cutting open the cartridges at the front without needing any further instrument prior to use. This cutting open action is to take place exactly at a right angle to the axis of the cartridge, that is to say in a radial plane, so that the cartridge is right to the front. The turning motion of the arresting member in this respect is a preferred possibility in connection with the knife, which then moves in a radial plane, and with the retainer hole into which the end of the cartridge is inserted. The radial plane of abutment leads to a defined point of cutting, i. e. to cutting at the same position in every case, and does not cause any undesired longitudinal thrust to be exerted on the cartridge during the turning motion.

In accordance with another convenient feature of the invention the catheter provided with the sleeve is loosely covered by a foil sheath of a thin protective foil which is shut off at the distal end but which may be torn open by a pull on it in a direction towards the proximal end and which has a tug grip at the proximal end. The foil sheath may have a lateral tag at the proximal end with one or more finger holes. These features facilitate handling of the equipment in such a manner as to avoid drawing in substances from the vagina of the animal being dealt with.

In accordance with a further feature of the invention there is an encircling shoulder in the catheter at a distance from the distal end which is somewhat less than the standard length of the sperm cartridges. This feature is useful when advancing the inserted cartridge and centering it in the conical longitudinal passage of the shaped member, if it is not possible to apply a sufficient longitudinal force with the plunger.

Further details, advantages and developments of the invention will be seen from the following detailed account of preferred working examples of the invention as shown in the drawings.

LIST OF THE SEVERAL VIEWS OF THE DRAWINGS

FIG. 4 is a longitudinal section through a modified form of the transfer device without showing the sleeve and the distal end thereof.

FIG. 5 is a front view of the device of FIG. 4 without the plunger.

FIG. 6 is a rear view of an arresting member as used in the device of FIG. 4.

DETAILED ACCOUNT OF WORKING EMBODIMENTS OF THE INVENTION

Figure 1:
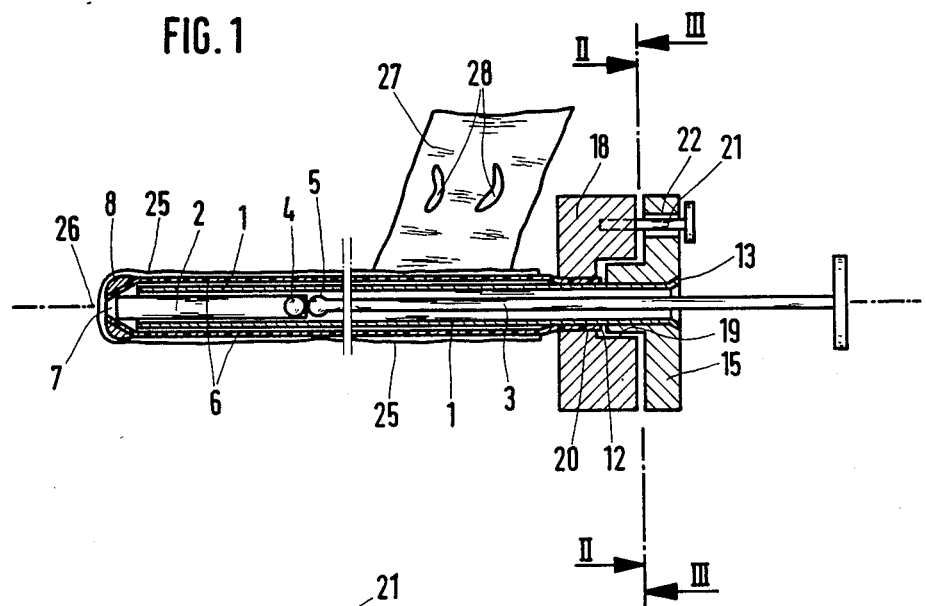
FIG. 1 is a longitudinal section of the transfer device in accordance with the invention for introduction into the body of an animal.
Figure 2:
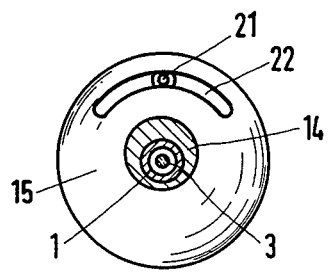
FIG. 2 is a section in a single plane looking in the direction II—II in FIG. 1.
Figure 3:
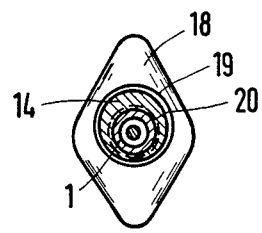
FIG. 3 is a section in the same plane looking in the direction III—III marked in FIG. 1.

The transfer device as shown in FIG. 1 is made up of a catheter 1 consisting of a thin-walled metal tube and in which for the purpose of transfer contains a cartridge 2 of material such as sperm and a plunger 3 with the aid of which the cartridge 2 is firstly thrust through as far as the distal end of the catheter 1 and a sealing and piston member in the form of a ball 4 located in the cartridge 2 is thrust forwards so as to squeeze out the contents of the cartridge. For this purpose the plunger 3 has a button-like head 5 at its distal end, which has a diameter matching the diameter of the cartridge to be used. In order to be able to squeeze out the contents of thin cartridges, which normally contain a piston in the form of a cotton plug, it is convenient to have two plungers with different thicknesses.

At the proximal end of the plunger there is a thumb plate. The transfer device furthermore has a sleeve 6 surrounding the catheter 1 like a casing. The sleeve consists of flexible plastic and is removed and replaced by a new or fresh sleeve every time the transfer device is used.

At its distal end the hose material as such of the sleeve 6 tapers conically to an opening and an annular shaped member 8 is bonded on the conical part. This shaped member has a conical bore adapted to the cone of the hose material and externally has a rounded form.

The purpose of this conical form of the interior space in the end piece of the sleeve 6, whose taper is such that tubular cartridges with a relatively small diameter are also able to be supported, is to ensure that the inserted cartridge 2 is accurately centered whatever its diameter and may be discharged through the opening 7. On using the plunger 3 to thrust the ball 4 forwards or using the head to thrust a cotton plug forwards the wall of the cartridge 2 and later the ball 4 or the head 5, respectively, itself presses internally against the cone without exerting any substantial force in the axial direction on the annular shaped member 8. Since this force is firstly exerted on the material of the wall of the sleeve 6 and then acts thereby on the annular shaped member 8 there is no danger of the shaped member becoming detached from the wall of the sleeve 6.

Since the supporting force, that is to say the force acting against the extruding force exerted by the plunger, is transmitted via the sleeve 6 the latter has to be anchored on the catheter 1 or a handle located thereon. This anchoring is provided at the proximal end 12 of the sleeve 6. The proximal end 13 of the catheter 1 is slightly crimped outwards at the end and a plastic tube 14 is bonded to this end. This tube 14 has an annular flange 15 on the proximal end. The plastic tube 14 is eccentrically mounted on the circularly cylindrical catheter 1 so that at this part of the periphery it has a thicker wall than at another, opposite part. An arresting member 18 is mounted on this plastic tube 14, which has a form able to be readily gripped, that is to say the form of a diamond and has two mutually eccentric longitudinal holes 19 and 20, the eccentricity of such holes in relation to each other preferably being equal in amount to the ratio of the plastic tube 14 to the catheter 1. The hole 19 has a diameter which is only a little larger than the external diameter of the plastic tube 14, that is to say by such an amount that the wall of the sleeve 6 may be introduced between the outer face of the catheter 1 and the inner diameter of the bore 20. By twisting the arresting member 18 on the plastic tube 14 owing to the eccentricity the inner wall face of the hole 20 is pressed into contact along a semicircular path against the outer face of the catheter 1, clamping the sleeve 6 inbetween. In this respect it is unimportant whether the proximal end 12 of the sleeve 6 is slit or not. As made clear, the difference in diameter between the catheter 1 and the bore 20 has to be sufficient to ensure that sleeves 6 matching the diameter of the catheter 1 or sleeves 6 with a greater diameter are able to be inserted, with or without the formation of folds. As will be clear the degree of eccentricity and the ratio of the diameters of the catheter 1 and of the hole or bore 20 are to match each other in order to achieve the desired firm clamping effect: in the case of an external diameter of the catheter of 3.75 mm the plastic tube 14 will have a diameter of 8 mm and an eccentricity of 1 mm. The wall thickness of the sleeve 6 amounts to 0.2 mm and the internal diameter of the bore 20 will be 4.8 mm.

A pin, in the present case a screw 21 with a head, extends from the flange 15 and extends through a guide slot 22 formed in the flange 15. This pin serves for additional guiding and limiting of the rotary motion of the arresting member 18 and it furthermore retains the arresting member 18 in the axial direction so that it is not able to become detached from the proximal end of the transfer device.

In the present working example thereof the transfer device further comprises a foil sheath which is in the form of a thin protective foil and surrounds the sleeve 6 from the distal end as far as a position just short of the proximal end and encases it. In this respect the opening 7 as well is initially sealed off by the foil sheath 25. Since the foil material may be readily torn at the distal end, such tearing possibly being facilitated if necessary by a line 26 of intentional weakness, on pulling back the foil sheath 25 its front end will be ruptured so that the opening 7 will be exposed. At its proximal end the foil sheath 25 has a tag 27 having two finger holes 28. Using this tag 27 and applying a counteracting force on the flange 15 it is possible for the foil sheath 25 to be pulled back and thus ruptured or torn open. Fouling of the sleeve 6, more particularly at its opening 7, during introduction of the transfer device is prevented if the foil sheath is only torn open at the front after the transfer device has been inserted so far that its distal end is already past those parts at which contamination is likely. It is convenient if the sleeves 6 are prefitted and stored with the foil sheath 25, which thus constitutes a sort of individual packing.

In the design shown in FIGS. 4 through 6 the device is furthermore provided with an integral snipping off device for cutting the tips of the cartridges. The cartridge cut open at the front end has to be in close contact with the inner cone of the cartridge at the distal end thereof, for which reason the cut surface has to be precisely in a radial plane of the circularly cylindrical cartridge. If scissors are used, possibly when the light is poor, there may often be difficulties.

As will be seen from FIG. 4, the flange 15 in this form of the invention is in the form of a bowl with a rib 31 in the wall of the bowl directed inwards and in which there is a retainer hole 32. The retainer hole has such a diameter that the conventional cartridges may be pushed through it and it is open at both its ends. At the parting plane between the flange 15 and the arresting member 18 there is a recess 33 in the part which moves past under the retainer hole 32 on turning the arresting member 18 and on the side facing the flange 15 there is a knife 34 whose cutting edge 35 has a radial component. The knife 34 is locked on the arresting member 18 so as to turn therewith and when the latter is turned within the limits determined by the guide slot 22 the cutting edge 35 will sweep across the full cross section of the opening of the retainer hole 32 adjacent to the arresting member 18.

The recess 33 has base surface 36 which is opposite to the opening facing it of the retainer hole. This base surface 36 is in a plane which is radial in relation to the axis of rotation of the arresting member 18 and thus does not have any axial component so that the during cutting of the inserted cartridge the latter does not come clear of the base surface 36 and does not have any thrust force transmitted to it.

This means that during the cutting action of the knife 34 the cartridges are always at precisely the same position in a radial plane without any separate instrument being required for this purpose.

Figure 7:
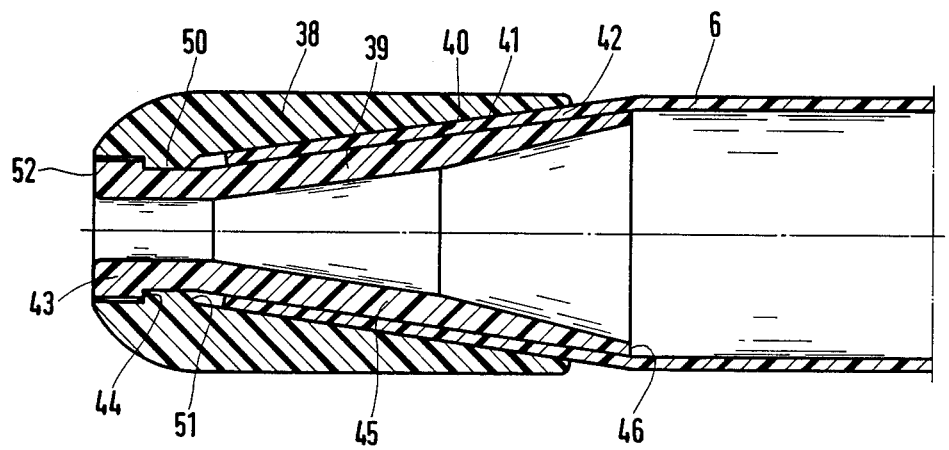
FIG. 7 is a longitudinal section through the distal sleeve end with a two-piece shaped member thereon as part of a further, modified form of the invention.

FIG. 7 shows the distal end of the sleeve 6 with the shaped member mounted thereon in a design with an external shaped member 38 and an internal shaped member 39. Between the conical inner wall face 40 of the external shaped member 38 and a conical outer wall face 41 of the internal shaped member 39, which have same conical angle, there is a narrow gap 42 in which the distal end of the sleeve 6 is clamped.

As a whole the inner shaped member is in the form of a conical tube which at its front or distal end has a cylindrical tubular spigot 43 with an outwardly directed detent shoulder 44 adjoining a conical tubular member 45, whose internal conical angle increases towards the end 46 of the inner shaped member 39 so that its wall thickness at the end 46 is small. On pulling the sleeve 6 onto the catheter 1 the end 46 abuts against the distal end face of the catheter, but however the inserted cartridge certainly does not lodge on the end 46 but is automatically centered on the conical inner wall face of the tubular member 45.

At its distal end the outer shaped member 38 has a non-conical longitudinal passage section with an inwardly directed peripheral rib 50, which towards the distal end has a radial face corresponding to the detent shoulder 44 and on the opposite side it has a conical face 51. In the assembled condition of the device the rib 50 abuts the detent shoulder 44 and owing to the relative sizes of the two shaped members the distal end face 52, which is composed of the faces of the two shaped members, is smooth and without any step therein.

The two shaped members 38 and 39 are made of an elastic plastic material with a smooth outer surface. The elasticity is responsible for a certain radial extensibility of the external shaped member 38 and a radial compressibility of the internal shaped member 39. For assembly the first step is for the sleeve 6 to be drawn onto the internal shaped member 39, if the sleeve 6 does in fact have a conically pointed form, there being a small degree of radial stretch. If it is a question of a plain cylindrical sleeve 6 the shaped member 39 is simply pushed into place. The subassembly consisting of the sleeve 6 and the internal shaped member 39 is now inserted into the wide opening of the external shaped member 38; in the case of a cylindrical sleeve 6 the latter will automatically take on a conical form in the gap 42 being formed. When during insertion the distal end surface of the shaped member 39 reaches the conical face 51 of the rib 50 the external shaped member 38 is compressed until after moving past the rib 50 owing to the detent shoulder 44 the shaped members resume their normal size and the completely assembled sleeve tip is securely joined together. Further forward sliding of the internal shaped member 39 is precluded by the contact of the wall faces 40 and 41 with the sleeve 6 between them. The sleeve 6 is so firmly clamped between these conical walls faces that there is no chance of its slipping out, more especially since the application of a thrust force on the internal shaped member 39 towards the distal end face 52 causes the clamping effect to become firmer and firmer.

The tip on the sleeve 6 made up of the two shaped members 38 and 39 and which consists of simple cheap plastic parts, is discarded after use like the sleeve 6.

As regards the centering of the cartridges with different diameters in the conical longitudinal passage in the shaped members there is, in addition to the use as mentioned of a respective plunger, also the possibility of employing a plunger suitable for the small-diameter cartridges, that is to say for 0.25 ml cartridges in accordance with the generally accepted French standard (entitled "paillettes fines") while for large-diameter cartridges, that is to say 0.5 ml cartridges conforming to the said French standard it is possible to center the cartridge using a peripheral shoulder (not shown) in the catheter by applying a force and to squeeze out its contents with the said thin plunger. Whereas in fact the thin plunger is sufficient to empty the cartridge, it would be unsuitable for centering the cartridge at its the outlet end, since when forward motion takes place it is not opposed by sufficient friction; 0.25 ml cartridges with half the standard length and twice the normal diameter (marketed under the designation of "Minitueb") normally contain a ball as a seal and a piston which is acted upon by the thin plunger and which under the action of a sufficient forward thrust on the wall on the cartridge wall is moved forwards in the cartridge.

Figure 8:
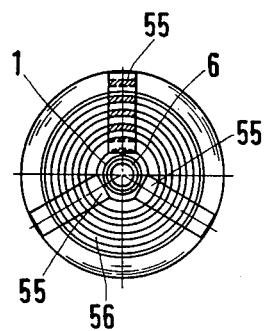
FIG. 8 is a section generally like that of FIG. 2 through a further form of the invention.

FIG. 8 shows an alternative design of the clamping device of FIGS. 1 through 5, namely a design using a three-jawed chuck whose three jaws 55 are able to be moved radially inwards or outwards by turning a spiral thread 56 so that when they are moved inwards they clamp the sleeve 6 at its proximal end onto the catheter. A single or two-jaw chuck would however also be suitable to hold the sleeve.

The transfer device makes it possible for a medical practitioner or a veterinary surgeon to use the above-described sleeves which may be neatly inserted and are suitable for a number of different cartridges of material to be administered, or indeed to use other forms of sleeve. Such other sleeves may for example be slit or smooth sleeves and furthermore the width of the sleeve is in no way critical so that the transfer device of the invention is of universal application.

We claim:
1. A transfer device for the administration of materials comprising:
 a hollow cylindrical catheter having a proximal end and a distal end, said proximal and distal ends being open;
 a tubular cartridge of material to be administered positioned within said catheter;
 a plunger being slidably disposed within said catheter through said proximal end for forcing the material within the cartridge out of the catheter through said distal end;
 a replaceable tubular sleeve having a proximal end and a distal end, said tubular sleeve being disposed around at least a portion of said catheter, said proximal end of said tubular sleeve being detachably secured to said proximal end of said catheter, said distal end of said sleeve being positioned adjacent said distal end of said catheter and being conically tapered and including a port for the emergency of the material to be administered;
 a radially symmetrical shaped member having a distal end and a proximal end and having a conically shaped longitudinal passage therein, said radially symmetrical shaped member being positioned around at least a portion of said distal end of said sleeve such that said conically shaped longitudinal passage received therein and complements said conically tapered distal end of said sleeve, said shaped member comprising an external member into which, in addition to the sleeve, an internal shaped member is inserted, said internal shaped member including a distal end and a proximal end and further including a conical external face with a degree of conicity corresponding to the conically shaped longitudinal passage in the external shaped member, said internal and external shaped members being positioned relative to each other such that said conical part of said sleeve is clamped between said conical external face of said internal member and said conically shaped longitudinal passage, said internal shaped member including a conical internal wall face, which tapers towards the distal ends of said shaped members.

2. The transfer device as claimed in claim 1 wherein both the external shaped member and the internal shaped member have meshing non-conical generally cylindrical internal and external faces located directly adjacent the distal ends of the external and internal shaped members.

3. The transfer device as claimed in claim 1 wherein the external shaped member and the internal shaped member are releasably coupled together.

4. The transfer device as claimed in claim 3 wherein the external shaped member and the internal shaped member have a detent coupling mechanism.

5. The transfer device as claimed in claim 1 wherein the external shaped member and the internal shaped member have distal end faces steplessly merging with each other.

6. The transfer device as claimed in claim 1 wherein the conical taper of the distal end of the sleeve is formed by compression and attachment of the shaped members between the conically shaped longitudinal passage of the external shaped member and the conical external face of the internal shaped member.

7. The transfer device as claimed in claim 1 wherein the internal shaped member includes a wall having a thickness, said distal end of said internal shaped member having a wall thickness which is greater than the wall thickness of said proximal end of said internal shaped member.

8. A transfer device for the administration of materials comprising:
  a hollow cylindrical catheter having a proximal end and a distal end, said proximal and distal ends being open;
  a tubular cartridge of material to be administered positioned within said catheter;
  a plunger being slidably disposed within said catheter through said proximal end for forcing the material within the cartridge out of the catheter through said distal end;
  a replaceable tubular sleeve having a proximal end and a distal end, said tubular sleeve being disposed around at least a portion of said catheter, said proximal end of said tubular sleeve being detachably secured to said proximal end of said catheter, said distal end of said sleeve being positioned adjacent said distal end of said catheter and being conically tapered and including a port for the emergency of the material to be administered;
  an eccentric gripping device positioned on the proximal end of the catheter, said eccentric gripping device compressing at least a part of the proximal end of said sleeve about the periphery of said proximal end of said catheter for securing said sleeve to said catheter, the eccentric gripping device including a support member eccentrically mounted on said catheter, said support member having a generally circular outer surface, an arresting member rotatably mounted on said support member, said arresting member including a first circular opening having a diameter slightly larger than the outer diameter of said support member for receiving said support member therein, said arresting member including a second circular opening having a diameter slightly larger than the diameter of said catheter for receiving said catheter therein such that said sleeve is positioned within said second opening between said arresting member and said catheter, said first and second openings being eccentrically offset such that said sleeve is compressed against the outer periphery of said catheter when said arresting member is rotated with respect to said support member; and
  a radially symmetrical shaped member having a distal end and a proximal end and having a conically shaped longitudinal passage therein, said radially symmetrical shaped member being positioned around at least a portion of said distal end of said sleeve such that said conically shaped longitudinal passage receives therein and complements said conically tapered distal end of said sleeve.

9. The transfer device as claimed in claim 8 wherein the support member is a cylindrical tube firmly secured on the catheter, said cylindrical tube having a varied wall thickness.

10. The transfer device as claimed in claim 9 wherein the catheter is in the form of a metal tube, said metal tube includes a crimped ring for securing said cylindrical tube thereon.

11. The transfer device as claimed in claim 9 wherein the cylindrical tube has a flange in which a circumferential track is formed and the arresting member has the form of a rotary handle and is provided with an axial projection which fits into the track of the flange, said track and axial projection cooperate to limit the rotational movement of said arresting member with respect to the cylindrical tube.

12. The transfer device as claimed in claim 11 wherein the flange comprises a retainer opening positioned parallel to the catheter axis and open at both ends, said arresting member including a knife positioned adjacent said retainer opening, wherein said arresting member can be positioned relative to the flange such that said knife partially or fully covers said retainer opening.

13. The transfer device as claimed in claim 12, wherein the knife is arranged in an end plane adjacent to the flange, said arresting member including a recess located under the knife, said recess being sized to complement the limited rotational movement of said arresting member.

* * * * *